US006680280B1

(12) United States Patent
Birke et al.

(10) Patent No.: US 6,680,280 B1
(45) Date of Patent: Jan. 20, 2004

(54) HYDROGENATING CATALYST CONTAINING NICKEL AND METHOD FOR PRODUCING THE SAME

(75) Inventors: Peter Birke, Langenbogen (DE); Reinhard Geyer, Halle (DE); Peter Kraak, Leipzig (DE); Rainer Schödel, Teutschenthal (DE)

(73) Assignee: Kataleuna GmbH Catalysts (DE)

( * ) Notice: Subject to any disclaimer, the term of this patent is extended or adjusted under 35 U.S.C. 154(b) by 0 days.

(21) Appl. No.: 09/914,557

(22) PCT Filed: Mar. 1, 2000

(86) PCT No.: PCT/EP00/01709

§ 371 (c)(1),
(2), (4) Date: Jan. 31, 2002

(87) PCT Pub. No.: WO00/51728

PCT Pub. Date: Sep. 8, 2000

(30) Foreign Application Priority Data

Mar. 3, 1999 (DE) ......................... 199 09 176

(51) Int. Cl.$^7$ .................... B01J 21/06; B01J 23/755
(52) U.S. Cl. ....................... 502/337; 502/259
(58) Field of Search ................ 502/337, 242, 502/259

(56) References Cited

U.S. PATENT DOCUMENTS

| 2,564,331 | A |   | 8/1951  | Hawley ................... 252/472 |
|-----------|---|---|---------|-----------------------------------|
| 3,700,745 | A | * | 10/1972 | Kovach et al. ......... 260/672 R  |
| 3,945,944 | A | * | 3/1976  | Kang .................... 252/455 R |
| 4,002,658 | A | * | 1/1977  | Dalla Betta et al. .... 260/449 M  |
| 4,026,823 | A | * | 5/1977  | Van Hook et al. .......... 252/472 |
| 4,073,750 | A | * | 2/1978  | Yates et al. .............. 252/459 |
| 4,090,980 | A |   | 5/1978  | Carter et al. ............. 252/477 |
| 4,160,745 | A | * | 7/1979  | Murrell et al. ........... 252/466 J|
| 4,253,991 | A | * | 3/1981  | Kanzler et al. ......... 252/455 R  |
| 4,454,026 | A | * | 6/1984  | Hensley, Jr. et al. .... 208/251 H |
| 4,597,908 | A |   | 7/1986  | Lok et al. .................... 260/409 |
| 4,668,654 | A | * | 5/1987  | Drake ........................ 502/242 |
| 4,670,416 | A |   | 6/1987  | Klimmek et al. ............. 502/259 |
| 4,916,030 | A | * | 4/1990  | Christodoulou et al. .... 428/614 |
| 4,956,328 | A |   | 9/1990  | Frohning et al. ........... 502/242 |
| 5,047,178 | A |   | 9/1991  | Ganguli et al. ............. 260/409 |
| 5,217,938 | A | * | 6/1993  | Reinada et al. ............. 502/325 |
| 5,320,998 | A | * | 6/1994  | Horiuchi et al. ............ 502/245 |
| 5,356,847 | A | * | 10/1994 | Henderson .................. 502/84 |
| 5,391,532 | A | * | 2/1995  | Soled et al. ................ 502/210 |
| 5,552,363 | A | * | 9/1996  | Pannell et al. .............. 502/337 |
| 5,705,723 | A | * | 1/1998  | Kallenbach et al. ........ 585/270 |
| 5,736,484 | A |   | 4/1998  | Polanek et al. ............. 502/349 |
| 5,773,657 | A | * | 6/1998  | Rutter et al. ................ 564/450 |
| 5,849,972 | A | * | 12/1998 | Vicari et al. ................ 585/531 |
| 5,916,838 | A | * | 6/1999  | Wulff-Doring et al. ..... 502/326 |
| 5,942,645 | A | * | 8/1999  | Rutter et al. ................ 568/832 |
| 5,977,013 | A | * | 11/1999 | Elliott et al. ................ 502/337 |
| 6,197,721 | B1| * | 3/2001  | Didillon et al. ............. 502/326 |
| 6,235,677 | B1| * | 5/2001  | Manzer et al. .............. 502/232 |

FOREIGN PATENT DOCUMENTS

| DE | 1257753   | 1/1968  |
| DE | 0152065   | 11/1981 |
| DE | 3537247   | 4/1987  |
| EP | 0089761   | 3/1983  |
| EP | 0098681   | 1/1984  |
| JP | 55-13333  | 1/1980  |
| SU | 283185    | 12/1970 |

* cited by examiner

Primary Examiner—Cam N. Nguyen
(74) Attorney, Agent, or Firm—Ostrolenk, Faber, Gerb & Soffen, LLP

(57) ABSTRACT

A hydrogenation catalyst and a process for its production, wherein the catalyst can be used for the hydrogenation of nitro groups in nitroaromatics to form the corresponding amines in the presence of water.

20 Claims, No Drawings

HYDROGENATING CATALYST CONTAINING NICKEL AND METHOD FOR PRODUCING THE SAME

DESCRIPTION

The invention relates to a catalyst which can be used in particular for the hydrogenation of nitro groups in nitroaromatics to form the corresponding amines in the presence of water, and to a process for its production.

The catalytic hydrogenation of nitroaromatics is known. The hydrogenation reactions are generally carried out both in a fixed-bed reactor and in a batch reactor. On an industrial scale, it is most usual to carry out hydrogenation reactions in the liquid phase with a suspended catalyst, the processes differing with regard to the reaction temperature, the pressure, the catalyst, the solvents and the way in which the reaction is carried out. The catalysts used are various catalyst systems, such as for example nickel-containing catalysts. For example, JP 551 33 33 describes the hydrogenation of 2,4-dinitrotoluene and 2,6-dinitrotoluene in the presence of the catalysts Pd/C, Raney nickel, Raney cobalt and/or platinum black.

EP A 98 681 has disclosed a nickel-kieselguhr supported catalyst for the hydrogenation of dinitrobenzophenone to form the corresponding diamine.

DE-A 3 537 247 describes the hydrogenation of dinitro compounds to form the diamines in the presence of modified Raney nickel catalysts.

DD 152 065 discloses the use of a nickel-$SiO_2$ catalyst with a special particle size distribution for the hydrogenation of nitro compounds.

EP-A 0 335 222 discloses the use of nickel-$Al_2O_3$/$ZrO_2$ supported catalysts for the hydrogenation of nitrites, aromatics, nitro compounds and olefins. This document discloses, inter alia, the simultaneous precipitation of nickel, zirconium and aluminum on supports at 50 to 1200° C. and at a pH of 7.3 to 9.0, activated carbon, $Al_2O_3$, $SiO_2$, kieselguhr and others being used as the supports.

SU patent 28 31 85 discloses nickel-$Al_2O_3$/$ZrO_2$ catalysts which have been produced by the precipitation of nickel and $Al_2O_3$ on $ZrO_2$.

According to the teaching of U.S. Pat. No. 2,564,331, a nickel-$ZrO_2$ catalyst is produced by precipitation of a nickel and zirconyl carbonate mixture with subsequent washing, drying and reduction at 250 to 3500° C., the catalyst containing at most 10% by mass of $ZrO_2$.

DE-B 1 257 753 discloses the precipitation of insoluble carbonates, the precipitation operation being initiated by evaporation of $CO_2$ and $NH_3$ out of a mixed salt solution of ammonium zirconyl carbonate and nickel amine carbonate.

EP-A 0 672 452 has disclosed catalysts for the hydrogenation of organic compounds which substantially contain 65 to 80% by mass of nickel, calculated as NiO, 10 to 25% by mass of $SiO_2$, 2 to 10% by mass of zirconium, calculated as $ZrO_2$, and 0 to 10% by mass of aluminum, calculated as $Al_2O_3$, the sum of the $SiO_2$ content and of the $Al_2O_3$ content being at least 15% by mass. These catalysts are produced by adding an acidic aqueous solution of Ni, Zr and, if desired, aluminum compounds to a basic aqueous solution or suspension of silicon compounds and, if desired, aluminum compounds. During the precipitation, the pH is initially reduced to 4.0 to 6.5 and is then set at 7 to 8. The precipitated product is dried, calcined and shaped.

The nickel hydrogenation catalysts which have been revealed hitherto all have the drawback that rapid aging of the catalysts takes place under the hydrothermal reaction conditions of the hydrogenation of nitroaromatics.

The technical problem on which the present invention is based is therefore that of providing nickel-containing supported catalysts which have a longer service life than the conventional catalysts in particular under the hydrothermal reaction conditions of the hydrogenation of nitroaromatics.

According to the invention, this problem is solved by the fact that a catalyst, in particular for the hydrogenation of nitro groups in nitroaromatics to form the corresponding amines in the presence of water, containing nickel on a support is provided, the catalyst being reduced and stabilized and having nickel crystallites with a bimodal nickel crystallite size distribution, a nickel content of from 60, in particular 61% by mass to 80% by mass (based on the total mass of the catalyst) and a degree of reduction of at least 70%. The degree of reduction is determined after further reduction of the stabilized catalyst for one hour at 100° C.

In a particularly preferred embodiment, the invention provides for the above-mentioned catalyst to have a bimodal nickel crystallite size distribution, the two maxima of the nickel crystallite size distribution lying at 30 to 80 Angstrom and 81 to 150 Angstrom. In a further particularly preferred embodiment, the invention provides for the proportion of nickel with a maximum of the nickel crystallite size distribution at 30 to 80 Angstrom to be ≧40% (based on the total mass of the catalyst). The proportion of metallic nickel with crystallites with a size of 30 to 80 Angstrom is therefore ≧40% (based on the total mass of the catalyst).

In a further preferred embodiment, it is provided that the above-mentioned catalyst is supported on a zirconium-containing support, preferably contains or consists of $ZrO_2$, $ZrO_2HfO_2$, $SiO_2.ZrO_2$, $SiO_2.ZrO_2HfO_2$ or mixtures of at least two of these substances.

In a particularly preferred embodiment, the $SiO_2$ content is 0 to 20% by mass (based on the total mass of the catalyst). In a further preferred embodiment, the $ZrO_2$ content is 20 to 40% by mass (based on the total mass of the catalyst). In a further preferred embodiment, the $HfO_2$ content is 0 to 4% by mass (based on the total mass of the catalyst).

In a particularly preferred embodiment of the invention, the reduced and stabilized catalysts may be used as powders with grain sizes of from 1 to 100 μm, preferably from 2 to 25 μm. Naturally, compacts can also be used.

The catalysts according to the invention are advantageously and surprisingly distinguished by their service life, which is longer than that of conventional catalysts while achieving a catalytic activity which is identical or better. Catalysts with the bimodal nickel crystallite size distribution according to the invention have a considerably longer service life than conventional catalysts, in particular under hydrothermal reaction conditions.

In the context of the present invention, the term bimodal nickel crystallite size distribution is understood as meaning a distribution of the nickel crystallites in which there are two maxima of the crystallite size distribution which can be clearly distinguished from one another.

In the context of the present invention, the term degree of reduction is understood as meaning the proportion of metallic nickel in the total nickel content of the catalyst in % after further reduction of the stabilized catalyst for one hour at 1000° C.

In a further embodiment, the invention also relates to a process for producing the above-mentioned catalyst. The invention therefore also relates to a process for producing a nickel-containing supported catalyst, in particular a catalyst for the hydrogenation of nitro groups in nitroaromatics to form the corresponding amines in the presence of water, in which, by precipitation from a solution which contains $Ni^{2+}$ and $Zr^{4+}$ with a basic solution, in particular a solution of NaOH, $NaHCO_3$ or $Na_2Co_3$ or a mixture of at least two of these substances, to a pH of 8 to 9, a precipitated product is obtained which is calcined at temperatures of from 250° C. to 650° C., is then rendered inert if appropriate, and is then reduced with hydrogen at temperatures of from 250° C. to 555° C., in particular 300° C. to 550° C., if appropriate rendered inert and then stabilized.

In a particularly preferred embodiment, the solution which contains $Ni^{2+}$ and $Zr^{4+}$ additionally contains $Hf^{4+}$. In a further preferred embodiment, the solution which contains $Ni^{2+}$ and $Zr^{4+}$ or the solution which contains $Ni^{2+}$ and $Zr^{4+}/Hf^{4+}$ also contains silicon dioxide $SiO_2$, preferably in suspended form. In a preferred embodiment, it is possible for the solution which contains $Ni^{2+}$ and $Zr^{4+}$ also to contain nitrates, in particular in the form of zirconyl nitrate.

The precipitated product is therefore produced by adding the above-mentioned basic solution to the solution which contains $Ni^{2+}$ and $Zr^{4+}$, this addition taking place until the mixture of the two solutions reaches a final pH of 8 to 9.

In a preferred embodiment, the invention provides for the precipitation to take place at temperatures of from 500° C. to 950C. In a preferred configuration, it is possible for the suspension obtained after the precipitation has been carried out, i.e. after the final pH has been reached, to continue to be stirred for, by way of example, one to two hours before further processing takes place.

In a further refinement, the invention relates to a process as described above in which the precipitated product, after the precipitation, is filtered, washed, preferably with water, and then dried at temperatures of from 110° C. to 150° C. in a nonreducing atmosphere, and a precursor catalyst is obtained.

In the context of the present invention, the term precursor catalyst is understood as meaning a product which is obtained after the precipitation of the starting components, i.e. of the solution which contains $Ni^{2+}$ and $Zr^{4+}$, and if appropriate $Hf^{4+}$, and, if appropriate, the $SiO_2$ with the added basic solution, filtration, washing with water and drying at temperatures in a nonreducing atmosphere.

According to the invention, the production of the precursor catalyst results in phases of nickelhydroxynitrate ($Ni_3(OH)_4(NO_3)_2$) or phases which contain nickelhydroxynitrate ($Ni_3(OH)_4(NO_3)_2$) in particular mixtures of nickelhydroxynitrate ($Ni_3(OH)_4(NO_3)_2$), nickelhydroxycarbonate ($Ni_2(OH)_2CO_3.4H_2O$) and nickelhydroxysilicate ($Ni_3Si_2O_5(OH)_4$) or mixtures of nickelhydroxynitrate ($Ni_3(OH)_4(NO_3)_2$) and nickel hydrogen carbonate ($Ni(HCO_3)_2$) or mixtures of nickelhydroxynitrate ($Ni_3(OH)_4(NO_3)_2$) and nickel hydroxide ($Ni(OH)_2$) with lattice expansions.

In the context of the present invention, the term lattice expansion is understood as meaning a shift in the interference point toward smaller angles.

Either before or after the calcining, the catalyst precursor may be shaped into tablets, extrudates, cushions, spheres or the like.

According to the invention, the reduction of the calcined product may take place both on the powder and on the compacts. According to the invention, it is particularly preferable if gas loads in the range from 500 to 3000 v/v h are used during the reduction.

In a preferred embodiment of the invention, there is provision for the catalysts to be stabilized after the reduction, preferably with an $O_2$—$N_2$—$CO_2$ mixture.

The invention therefore also relates to the provision of a process for passivating a catalyst according to the invention, which has preferably been reduced and/or has preferably been rendered inert, in which process the catalyst, in a process step a), is treated for at least 30 minutes in a $CO_2$—$N_2$ gas mixture with a $CO_2$ content of from 0.5 to 10% by volume at temperatures of from 91° C. to 350° C., then, in a process step b), is cooled, in the gas mixture referred to in step a), to a temperature of at most 90° C., then, in a process step c), after the temperature of at most 90° C. has been reached, in a first passivation phase oxygen, preferably air, is added to the gas mixture up to an oxygen content of 0.2 to 1.5% by volume of oxygen, and the catalyst is treated for at least 30 minutes with shaking in this mixture and then, in a process step d), the $CO_2$ content in the gas mixture described in step c) is reduced, in a second passivation phase, to<0.1% by volume and the $O_2$ content is increased to 1.5 to 21% by volume.

The procedure according to the invention for stabilizing the catalyst has the advantage of short stabilization times, while at the same time easily reactivatable catalysts of very good thermal stability are obtained. Advantageously, the catalysts are particularly uniformly passivated. Actually, it was surprising that catalysts which can be reactivated very uniformly and easily were obtained by the treatment with low-$CO_2$ inert gases under the conditions described.

In a preferred embodiment, the invention relates to a process as described above in which at least the passivation is carried out continuously or batchwise in a catalyst bed, in particular using a catalyst bed whose height to diameter ratio is in the range from 0.05 to 1.

In a further preferred embodiment, the invention provides a process as described above in which the concentration of the $CO_2$ during the treatment with the $CO_2$—$N_2$ mixture in accordance with process step a) is from 1 to 2.5% by volume.

In a further preferred embodiment, the invention provides a process as described above in which the gas load during the treatment with the $CO_2$—$N_2$ mixture as described in process step a) is 500 to 10000 v/v h. In a further preferred embodiment, the invention provides for the above-mentioned process to use a gas load during the treatment with the $CO_2$—$N_2$ mixture as described in process step a) and/or during the treatment with the $CO_2$—$N_2$—$O_2$ gas mixture as described in process steps c) and d) of 100 to 3000 v/v h.

In a further preferred embodiment, the invention provides for the treatment in the $CO_2$—$N_2$—$O_2$ gas mixture as described in process steps c) and d) of the above-mentioned process to be carried out for a period of from 30 minutes to 8 hours.

In a further refinement, the invention relates to a process as described above, in which the duration of the treatment as described in process step c), i.e. of the first passivation phase, is in the ratio of 9:1 with respect to the duration of the process step described in process step d), i.e. the second passivation phase.

In a further preferred embodiment, the invention relates to a process as described above in which the temperature of the treatment of the catalyst with the $CO_2$—$N_2$—$O_2$ gas mixture as described in step c), and/or step d) is 50 to 70° C.

In a further preferred embodiment, the invention provides a process as described above in which the $CO_2$ concentration in the $CO_2$—$N_2$—$O_2$ gas mixture during the treatment as described in process step c) is from 0.5 to 1.5% by volume. The invention can in a preferred way provide for the $CO_2$ content of the mixture from step a) to be reduced in order to carry out step c), for example to the range described above.

According to a further preferred refinement of the present invention, a process as described above is provided, in which the $O_2$ concentration in the $CO_2$—$N_2$—$O_2$ gas mixture during the treatment described in process step c) is from 0.25 to 0.8% by volume.

In a further preferred refinement of the invention, the $O_2$ concentration during the treatment described in process step d) is from 5 to 10% by volume.

In a further configuration, the invention relates to a process as described above in which it is provided that the shaking of the catalyst bed as described in process steps c) and/or d) is carried out at intervals of 10 to 20 minutes for a period of in each case 0.5 to 2 minutes. It is advantageous to set shaking frequencies of 10 to 50 Hz.

Naturally, it is also possible, in particular in the case of catalysts in powder form and catalysts with very high strengths, for the catalyst bed to be set in motion by producing a fluidized bed or by arranging it in a rotary tubular furnace. One significant aspect of the present invention is that of moving the catalyst at least from time to time during the passivation phases in accordance with process steps c) and d) in the oxygen-carbon dioxide-nitrogen mixture, for example in a moving bed.

In a particularly preferred manner, the stabilization can also be carried out by stabilizing in a stream of nitrogen with an oxygen content of from 0.1 to 1% by volume and a $CO_2$ content of 0.6% by volume at temperatures of less than 80° C.

Naturally, it is possible for the stabilization of the reduced catalyst obtained according to the invention also to be carried out in other ways, for example in accordance with the teaching of U.S. Pat. No. 4,090,980, which is incorporated in the disclosure of the present application with regard to the process parameters used to stabilize catalysts.

The invention is explained in more detail with reference to the following examples:

EXAMPLE 1

According to the Invention 4.5 l of water are placed in a heatable precipitation vessel which is provided with a stirrer, and then a metal nitrate solution, which as well as 400 g of nickel also contains zirconium in the form of a zirconyl nitrate solution, is added. The molar ratio of nickel to $ZrO_2$ in the metal nitrate solution is approx. 6. After the metal nitrate solution has been added, the mixture is heated to a temperature of 60° C. with stirring, and is then precipitated with an aqueous NaOH solution, which has been produced by dissolving 600 g of sodium hydroxide in 8 l of water, at temperatures of 60° C. until a pH of 8 to 8.5 is reached. The precipitation time is two hours. Following the precipitation, the suspension is stirred for a further approximately two hours at the above temperatures, is then filtered and is washed with alkali-free water until the $Na_2O$ content in the filter cake is<0.3% based on the residue on ignition of the filter cake which has undergone heat treatment at 800° C. The filter cake is then dried for approx. 15 hours at temperatures of from 120 to 150° C. and is calcined at 350° C.

The X-ray phase analysis of the dried intermediate product substantially showed a mixture of nickelhydroxynitrate ($Ni_3(OH)_4(NO_3)_2$) and $Ni(OH)_2$.

After the calcining, the dried intermediate product is milled, tabletted, rendered inert in a stream of nitrogen (1000 v/v h), heated in a stream of hydrogen (1000 v/v h) to 450° C. with a heat-up rate of 5° C./min and is reduced at 450° C. for 6 h. Then, the product was rendered inert for 30 min at 450° C. in the stream of nitrogen at 1500 v/v h, then cooled in the stream of nitrogen (1500 v/v h) to 280° C., then carbon dioxide is added to the nitrogen at this temperature, in a quantity which is such that the $CO_2$ concentration is 2% by volume. The catalyst is treated with this mixture for 30 minutes at 280° C., is then cooled to 55° C. in the same gas mixture and is stabilized in a stream of nitrogen (1500 v/v h) with an oxygen content of from 0.1 to 1% by volume and a $CO_2$ content of 0.6% by volume at temperatures of less than 80° C. The oxygen concentration was selected in such a way that the catalyst temperature did not exceed 80° C. The stabilization time at temperatures of <80° C. was 4 h. The degree of reduction of the catalyst after further reduction for one hour at 100° C. is 84%.

The reduced and stabilized catalyst contains approx. 60% of nickel and 30% of $ZrO_2$, based on the total mass of the catalyst.

It has a bimodal nickel crystallite size distribution. The maxima of the crystallite sizes lie at 52 Angstrom and 107 Angstrom. The proportion of finely dispersed nickel, i.e. nickel with crystallite sizes of from 30 to 80 Angstrom, is approx. 61%. The results of the catalytic measurements are given in the table.

EXAMPLE 2

According to the Invention 8 l of water and a solution of sodium silicate (60 g/l) are placed in the heatable precipitation vessel, and then a combined nickel/zirconyl nitrate solution (molar ratio: nickel/$ZrO_2$/$SiO_2$=1:0.13:0.065) is added with stirring. The mixture is then heated with stirring to a temperature of 75–80° C., and the precipitation is commenced by adding an aqueous soda solution (150 g of soda/l of solution). The precipitation has finished when the pH of 8–8.5 is reached. After precipitation for one hour, the finished precipitated suspension is stirred for a further 2 hours and is processed further as described in Example 1. The calcining of the dried material was carried out at 450° C.

X-ray analysis of the dried intermediate product revealed a mixture of nickelhydroxynitrate ($Ni_3(OH)_4(NO_3)_2$), nickelhydroxycarbonate ($Ni_2(OH)_2CO_3.4H_2O$) and nickelhydroxy-silicate ($Ni_3Si_2O_5(OH)_4$).

The further processing of the precipitated product was carried out as in Example 1. The finished catalyst contains approx. 65% of nickel, 18% of $ZrO_2$ and 3% of $SiO_2$, based on the overall catalyst. It had a bimodal nickel crystallite size distribution. The maxima of the crystallite sizes were at 49 Angstrom and 112 Angstrom. The proportion of finely dispersed nickel, i.e. nickel with crystallite sizes of 30 to 80 Angstrom, is approx. 54%. After further reduction for one hour in the stream of hydrogen (load: 1000 v/v h) at 100° C., the catalyst has a degree of reduction of 75%.

The results of the catalytic testing are shown in the table.

EXAMPLE 3

According to the Invention 6 l of water are placed in the precipitation vessel, and then a metal nitrate solution, which in addition to nickel and zirconium in the form of the nitrates, also contains kieselguhr as $SiO_2$ support, is added. The molar ratio of nickel/$ZrO_2$/$SiO_2$ in the metal nitrate/support suspension was 1:0.14:0.1. After a temperature of 90° C. has been reached, the precipitation is carried out by adding a sodium bicarbonate solution, which has been produced by dissolving 1.35 kg of NaHCO$_3$ in 10 l of water. After the precipitation temperature of 90° C. has been reached, the precipitation is commenced. The precipitation time is one hour. After the final pH of 8.5 has been reached, the finished precipitated suspension is stirred for a further two hours at 90° C. and is then processed further as described in Examples 1 and 2. The calcining of the dried material was carried out at temperatures of from 430 to 450° C. The reduction was carried out under the same conditions as in Example 1.

The X-ray examination of the dried intermediate product revealed a mixture of nickelhydroxynitrate (Ni$_3$(OH)$_4$(NO$_3$)$_2$), nickelhydroxycarbonate (Ni$_2$(OH)$_2$CO$_3$.4H$_2$O) and nickelhydroxysilicate (Ni$_3$Si$_2$O$_5$(OH)$_4$).

The finished catalyst contains approx. 60% of nickel, 16% of ZrO$_2$ and 5% of SiO$_2$ based on the total catalyst. The maxima of the crystallite sizes were at 44 Angstrom and 101 Angstrom. The proportion of finely dispersed nickel, i.e. with crystallite sizes of from 30 to 80 Angstrom, is approx. 62%.

After further reduction for one hour in a stream of hydrogen at 100° C., the catalyst has a degree of reduction of 81%.

The results of the catalytic testing are given in the table.

EXAMPLE 4

Comparative Example 305.76 g of Ni(NO$_3$)$_2$.6H$_2$O and 29.52 9 of Al(NO$_3$)$_3$. 9 H$_2$O are dissolved in 1760 ml of distilled water and 2.32 g of zirconylcarbonate in 9 ml of HNO$_3$ (56% by mass). The two solutions are combined and heated to 101° C. This mixed salt solution is added uniformly over the course of three minutes to a soda solution which is at a temperature of 100° C., is intensively stirred and has been produced from 147.04 g of Na$_2$CO$_3$ and 1416 ml of distilled water. 27.76 g of kieselguhr are stirred into the freshly precipitated suspension, and the mixture formed is stirred for a further three minutes.

The precipitated product is then filtered and washed with water at a temperature of 70° C., until the alkali content of the washing water is approx. 20 mg of Na$_2$O/l.

The filter cake obtained in this way is suspended in water at a temperature of 70° C. (filter cake to water quantitative ratio=1:1), stirred for 60 minutes and then filtered again. The filter cake which then forms is filtered again. The filter cake which forms is extruded to form cylindrical shaped bodies (diameter 5 mm, length 8 to 10 mm), and is then dried at a rising temperature (50 to 60° C.) with air to a residual water content of<10% by mass, based on dried mass. The dried material is reduced in the stream of hydrogen with a load of 400 v/v h at 470° C. for a period of four hours.

The phases takovite (carbonate variant) and nickelhydroxysilicate with incorporated carbonate were detected.

The stabilization was carried out as in the examples according to the invention. The properties of the catalyst are compared with those of the catalysts according to the invention in the table.

EXAMPLE 5

The catalytic characterization of the catalysts was carried out under the following conditions:

Hydrogenation of nitrobenzene to form aniline in a 0.5 l stirred autoclave with hydrogen consumption measurement at constant pressure:

Catalyst quantity: 0.25 g

Reaction mixture: 80 g of nitrobenzene and 40 ml of H$_2$O

Reaction pressure: 30 bar

Reaction temperature: 130° C.

Stirring rate: 2000 rpm

The time required to convert 100% of the nitrobenzene was used as a measure of the hydrogenation activity. The stability of the catalysts was characterized by the increase in the mean Ni crystallite size after the catalyst had been treated for 100 hours under the conditions of the catalytic test after the conclusion of the conversion of the nitrobenzene into aniline.

The XRD wide-angle scans for qualitative phase assignment were carried out under the following experimental recording conditions on a measurement station produced by Rich. Seifert & Co. Freiberger Präzisionsmechanik GmbH:

Generator data: 34 kV/30 mA

Goniometer: HZG4

Radiation: Cu—K$_a$

Filter: curved graphite monochromator

Angle range: 2Θ=10°–70°

Step width: ΔΘ=0.05°

Counting time: 4 s

The data were processed in the evaluation file APX63 (SEIFERT FPM). The JCPDS evaluation file 1997 was used to assign the crystalline structures.

The mean primary particle size of the nickel was also determined using a measurement station produced by Rich. Seifert & Co. Freiberger Prazisionsmechanik GmbH, with the scatter curve sections perpendicular to the (111) lattice plane being recorded from the interference band broadening under the following conditions:

Generator data: 40 kV/30 mA

Goniometer: XRD7

Radiation: Cu—K$_a$

Filter: Ni

Angle range: 2Θ=41°–49°

Step width: ΔΘ=0.05°

Counting time: 20 s

Conclusions about the modality (monomodal Gaussian line profile or bimodal Gaussian line profile) of the Ni (111) line profile were obtained by applying the peak disentangling program PF4 produced by Jandel Corporation.

The measured data in the table demonstrate the advantages of the catalysts according to the invention: a high catalytic activity and very good stabilization properties, as indicated by the low increases in the Ni crystallite size.

TABLE

| Catalyst | Reaction time for 100% conversion | Yield of aniline in % | Mean Ni crystallite size in Angstrom (before the reaction) | Mean Ni crystallite size in Angstrom (after the stability test) |
| --- | --- | --- | --- | --- |
| Example 1 according to the invention | 86 | 99.9 | 73 | 83 |
| Example 2 according to the invention | 88 | 99.85 | 78 | 91 |
| Example 3 according to the invention | 84 | 99.9 | 66 | 79 |
| Example 4 comparative example | 121 | 99.8 | 107 | 138 |

What is claimed is:

1. A catalyst for the hydrogenation of nitro groups in nitroaromatics, comprising nickel on a zirconium-containing support, wherein the catalyst is stabilized and has nickel crystallites with a bimodal nickel crystallite size distribution, a nickel content of 60 to 80% by mass based on the total mass of the catalyst, a $ZrO_2$ content of 20 to 40% by mass based on the total mass of the catalyst, and a degree of reduction after reduction for one hour at 100° C. of at least 70%.

2. The catalyst as claimed in claim 1, wherein the two maxima of the nickel crystallite size distribution lie at 30 to 80 Angstroms and 81 to 150 Angstroms.

3. The catalyst as claimed in claim 2, wherein the proportion of the nickel with crystallite sizes of from 30 to 80 Angstroms is at least 40% by mass based on the total mass of the catalyst.

4. The catalyst as claimed in claim 1, wherein the support is at least one of $ZrO_2$, $ZrO_2HfO_2$, $SiO_2.ZrO_2$ and $SiO_2.ZrO_2HfO_2$.

5. The catalyst as claimed in claim 4, wherein the $SiO_2$ content does not exceed 20% by mass based on the total mass of the catalyst.

6. The catalyst as claimed in claim 4, wherein the $HfO_2$ content does not exceed 4% by mass based on the total mass of the catalyst.

7. The catalyst as claimed in claim 1, in the form of a powder having grain sizes of from 1 to 100 $\mu$m.

8. The catalyst as claimed in claim 3, wherein the powder has grain sizes of 2 to 25 $\mu$m.

9. The catalyst as claimed in claim 7, wherein the two maxima of the nickel crystallite size distribution lie at 30 to 80 Angstroms and 81 to 150 Angstroms, the proportion of the nickel with crystallite sizes of from 30 to 80 Angstroms is at least 40% by mass based on the total mass of the catalyst, the support is at least one of $ZrO_2$, $ZrO_2HfO_2$, $SiO_2.ZrO_2$ and $SiO_2.ZrO_2HfO_2$, wherein the $SiO_2$ content does not exceed 20% by mass based on the total mass of the catalyst, and the $HfO_2$ content does not exceed 4% by mass based on the total mass of the catalyst.

10. A process for producing a nickel-containing supported catalyst for the hydrogenation of nitro groups in nitroaromatics as claimed in claim 1, comprises forming a precipitate by combining of a solution which contains $Ni^{2+}$ and $Zr^{4+}$ and a basic solution to produce a final pH of 8 to 9, calcining the precipitate at a temperature from 250° C. to 650° C., reducing the calcined precipitate with hydrogen at a temperature from 250° C. to 550° C., and stabilizing the reduced calcined precipitate.

11. The process as claimed in claim 10, wherein the calcined precipitate is rendered inert before it is reduced.

12. The process as claimed in claim 10, wherein the basic solution is a solution of at least one of NaOH, $NaHCO_3$ and $Na_2CO_3$.

13. The process as claimed in claim 10, wherein the solution which contains $Ni^{2+}$ and $Zr^{4+}$ contains at least one of $NO^{3-}$, $Hf^{4+}$ and $SiO_2$.

14. The process of claim 10, wherein the formation of the precipitate is effected at a temperature from 50 to 95° C.

15. The process as claimed in claim 10, wherein, prior to the calcination, the precipitate is filtered from the solution, washed and dried in a non-reducing atmosphere to obtain a catalyst precursor.

16. The process as claimed in claim 15 wherein the catalyst precursor contains nickelhydroxynitrate.

17. The process as claimed in claim 15, wherein the catalyst precursor is shaped into a tablet, extrudate, cushion or sphere before or after calcination.

18. The process as claimed in claim 10, wherein reduction is carried out at a gas load of 500 to 3,000 v/v h, and the stabilization is effected at a temperature of less than 80° C.

19. The process as claimed in claim 10, wherein the catalyst is stabilized by contact with a mixture consisting of $O_2$, $N_2$ and $CO_2$.

20. The process as claimed in claim 10, wherein the solution containing $Ni^{2+}$ and $Zr^{4+}$ contains at least one of $NO^{3-}$, $Hf^{4+}$ and $SiO_2$ is combined with the basic solution which contains at least one of NaOH, $NaHCO_3$ and $Na_2CO_3$ at a temperature from 50 to 95° C.; the precipitate is filtered from the solution, washed with water and dried in a non-reducing atmosphere at a temperature from 110–150° C. to obtain a catalyst precursor containing nickelhydroxynitrate; the catalyst precursor is shaped into a tablet, extrudate, cushion or sphere before or after the calcining; wherein the precipitate is rendered inert after the calcining and before the reduction; reduction is carried out at a gas load of 500 to 3,000 v/v h; and the reduced catalyst is stabilized at a temperature of less than 80° C. with a gas mixture comprising nitrogen, oxygen and carbon dioxide.

* * * * *